US00PP17439P2

(12) United States Plant Patent
Smith

(10) Patent No.: US PP17,439 P2
(45) Date of Patent: Feb. 20, 2007

(54) ***CHRYSANTHEMUM* PLANT NAMED 'YOMICHELLE'**

(50) Latin Name: *Chrysanthemum×morifolium*
Varietal Denomination: Yomichelle

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 30 days.

(21) Appl. No.: 11/157,411

(22) Filed: Jun. 21, 2005

(51) Int. Cl.
*A01H 5/00* (2006.01)

(52) U.S. Cl. ..... Plt./295

(58) Field of Classification Search ..... Plt./295
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Yomichelle', characterized by its compact, upright and somewhat outwardly spreading plant habit; freely branching habit; dense and full plant habit; uniform and freely flowering habit; daisy-type inflorescences with elongated oblong-shaped ray florets; yellow bronze-colored ray florets; and natural season flowering in early September in the Northern Hemisphere.

1 Drawing Sheet

Botanical designation: *Chrysanthemum×morifolium.*
Cultivar denomination: 'Yomichelle'.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Yomichelle'.

The new cultivar is a product of a planned breeding program conducted by the Inventor in Gainesville and Alva, Fla. The objective of the breeding program is to create new garden-type *Chrysanthemum* cultivars having inflorescences with desirable inflorescence forms, attractive floret colors and good garden performance.

The new *Chrysanthemum* originated from a cross-pollination made in March, 2001 in Gainesville, Fla., of the *Chrysanthemum×morifolium* cultivar Atlantico, not patented, as the female, or seed, parent with the *Chrysanthemum×morifolium* cultivar Stacy, disclosed in U.S. Plant Pat. No. 11,852, as the male, or pollen, parent. The new *Chrysanthemum* was discovered and selected by the Inventor as a single flowering plant within the progeny of the stated cross-pollination grown in a controlled environment in Alva, Fla. in September, 2001. The selection of this plant was based on its desirable inflorescence form, attractive floret coloration and good garden performance.

Asexual reproduction of the new cultivar by terminal vegetative cuttings taken in a controlled environment in Alva, Fla. since January, 2002, has shown that the unique features of this new *Chrysanthemum* are stable and reproduced true to type in successive generations.

SUMMARY OF THE INVENTION

The cultivar Yomichelle has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yomichelle'. These characteristics in combination distinguish 'Yomichelle' as a new and distinct cultivar:

1. Compact, upright and somewhat outwardly spreading plant habit.
2. Freely branching habit; dense and full plants.
3. Uniform and freely flowering habit.
4. Daisy-type inflorescences with elongated oblong-shaped ray florets.
5. Yellow bronze-colored ray florets.
6. Natural season flowering in early September in the Northern Hemisphere.

In side-by-side comparisons conducted in Alva, Fla., plants of the new *Chrysanthemum* differed from plants of the female parent, the cultivar Atlantico, in the following characteristics:

1. Plants of the new *Chrysanthemum* were slightly smaller than plants of the cultivar Atlantico.
2. Plants of the new *Chrysanthemum* flowered about two weeks earlier than plants of the cultivar Atlantico when grown under natural season conditions.
3. Plants of the new *Chrysanthemum* had larger inflorescences than plants of the cultivar Atlantico.
4. Ray florets of plants of the new *Chrysanthemum* resisted fading longer than ray florets of plants of the cultivar Atlantico.

In side-by-side comparisons conducted in Alva, Fla., plants of the new *Chrysanthemum* differed from plants of the male parent, the cultivar Stacy, in the following characteristics:

1. Plants of the new *Chrysanthemum* were stronger than and not as mounding as plants of the cultivar Stacy.
2. Plants of the new *Chrysanthemum* flowered about two weeks earlier than plants of the cultivar Stacy.

3. Plants of the new *Chrysanthemum* flowered more uniformly than plants of the cultivar Stacy.
4. Plants of the new *Chrysanthemum* had smaller inflorescences than plants of the cultivar Stacy.
5. Plants of the new *Chrysanthemum* and the cultivar Stacy differed in ray floret color as plants of the cultivar Stacy had white-colored ray florets with purple-colored apices.

Plants of the new *Chrysanthemum* can be compared to plants of the *Chrysanthemum* cultivar Golden Grace, disclosed in U.S. Plant Pat. No. 8,785. In side-by-side comparisons conducted in Alva, Fla., plants of the new *Chrysanthemum* differed from plants of the cultivar Golden Grace in the following characteristics:

1. Plants of the new *Chrysanthemum* were smaller and more rounded than plants of the cultivar Golden Grace.
2. Plants of the new *Chrysanthemum* flowered more uniformly than plants of the cultivar Golden Grace.
3. Ray florets of plants of the new *Chrysanthemum* were darker in color when opening than ray florets of plants of the cultivar Golden Grace.

Plants of the new *Chrysanthemum* can also be compared to plants of the *Chrysanthemum* cultivar Phoebe, not patented. In side-by-side comparisons conducted in Alva, Fla., plants of the new *Chrysanthemum* differed from plants of the cultivar Phoebe in the following characteristics:

1. Plants of the new *Chrysanthemum* had larger inflorescences than plants of the cultivar Phoebe.
2. Ray florets of plants of the new *Chrysanthemum* were darker in color when opening than ray florets of plants of the cultivar Phoebe.

BRIEF DESCRIPTION OF THE PHOTOGRAPH

The accompanying photograph illustrates the overall appearance of the new *Chrysanthemum*. These photograph show the colors as true as it is reasonably possible to obtain in colored reproductions of this type. Colors in the photograph may differ slightly from the color values cited in the detailed botanical description which accurately describe the colors of the new *Chrysanthemum*. The photograph comprises a side perspective view of a typical flowering plant of 'Yomichelle' grown in a container.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and early fall in an outdoor nursery under conditions and practices which approximate those generally used in commercial garden-type *Chrysanthemum* production. One cutting was planted in a 15.25-cm container in mid-July, 2004. Plants were grown under natural season conditions. During the production of the plants, temperatures ranged from 10° to 32° C. Measurements and numerical values represent averages for typical flowering plants.

Botanical classification: *Chrysanthemum×morifolium* cultivar Yomichelle.

Commercial classification: Daisy-type garden *Chrysanthemum*.

Parentage:

*Female, or seed, parent.*—*Chrysanthemum×morifolium* cultivar Atlantico, not patented.

*Male, or pollen, parent.*—*Chrysanthemum×morifolium* cultivar Stacy, disclosed in U.S. Plant Pat. No. 11,852.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous daisy-type garden *Chrysanthemum*. Inverted triangle with mounded crown. Stems initially upright, then somewhat outwardly spreading; compact growth habit. Freely branching with about 13 primary branches with lateral branches potentially forming at every node. Moderately vigorous.

*Plant height.*—About 22 cm.

*Plant diameter.*—About 33 cm.

*Lateral branches.*—Length: About 17.5 cm. Diameter: About 6 mm. Internode length: About 1.4 cm. Aspect: Upright and outwardly spreading. Texture: Pubescent. Color: Close to 146A.

*Foliage description.*—Leaf arrangement: Alternate. Length: About 3.3 cm. Width: About 3 cm. Apex: Mucronate. Base: Attenuate to truncate. Margin: Palmately lobed, sinuses mostly divergent. Texture, upper surface: Slightly pubescent. Texture, lower surface: Pubescent; veins prominent. Color: Developing and fully expanded foliage, upper surface: More darker green than 147A. Developing and fully expanded foliage, lower surface: Close to 147A. Venation, upper surface: More darker green than 147A. Venation, lower surface: Close to 147A. Petiole length: About 1.9 cm. Petiole diameter: About 2.5 mm. Petiole color, upper surface: Darker green than 147A. Petiole color, lower surface: Close to 147A.

Inflorescence description:

*Appearance.*—Daisy-type inflorescence form with elongated oblong-shaped ray florets. Inflorescences borne on terminals above foliage, arising from leaf axils. Ray florets developing acropetally on a capitulum. About seven inflorescences per lateral branch.

*Flowering response.*—Under natural season conditions, plants flower in early September in the Northern Hemisphere.

*Inflorescence bud (before showing color).*—Height: About 6 mm. Diameter: About 8 mm. Shape: Oblate. Color (lower surface of phyllaries): More green than 147A.

*Inflorescence size.*—Diameter: About 3.2 cm. Depth (height): About 8 mm. Disc diameter: About 9 mm. Receptacle diameter: About 4 mm.

*Ray florets.*—Shape: Elongated oblong. Length: About 1.5 cm. Width: About 5 mm. Corolla tube length: About 3 mm. Corolla tube diameter: About 1.5 mm. Apex: Emarginate. Margin: Fused. Texture: Smooth, glabrous; satiny. Surface: Concave to mostly flat to eventually slightly convex. Orientation: Initially upright, then slightly upright to perpendicular to the peduncle. Number of ray florets per inflorescence: About 28 in about two whorls. Color: When opening, upper surface: Close to 6A to 9A overlain with 46A. When opening, lower surface: Close to 6B to 9B.

Fully opened, upper surface: Close to 6A to 9A more faintly overlain with 46A. Fully opened, lower surface: Close to 6B to 9B.

*Disc florets.*—Shape: Tubular, elongated. Length: About 5 mm. Width, apex: About 1.25 mm. Width, base: Less than 1 mm. Number of disc florets per inflorescence: About 64. Color: Immature: Close to 6A to 9A. Mature: Apex: Close to 9A. Mid-section: Close to 144B. Base: Close to 155D.

*Phyllaries.*—Quantity per inflorescence: About 18. Length: About 6 mm. Width: About 2 mm. Shape: Ligulate. Apex: Acute. Base: Truncate. Margin: Entire. Texture, upper surface: Smooth, waxy. Texture, lower surface: Pubescent. Color, upper surface: More green than 146A. Color, lower surface: More green than 147A.

*Peduncle.*—Length: First peduncle: About 5 cm. Fourth peduncle: About 8.25 cm. Diameter: About 2 mm. Strength: Strong. Aspect: About 40° to 45° from vertical. Texture: Pubescent. Color: Close to 146A.

*Reproductive organs.*—Androecium: Present on disc florets only. Anther length: Less than 1 mm. Anther color: Close to 12A. Amount of pollen: None observed. Gynoecium: Present on both ray and disc florets. Style length: About 4 mm. Style color: Close to 154A. Stigma color: Close to 9A.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0° to more than 38° C.

It is claimed:

1. A new and distinct cultivar of *Chrysanthemum* plant named 'Yomichelle', as illustrated and described.

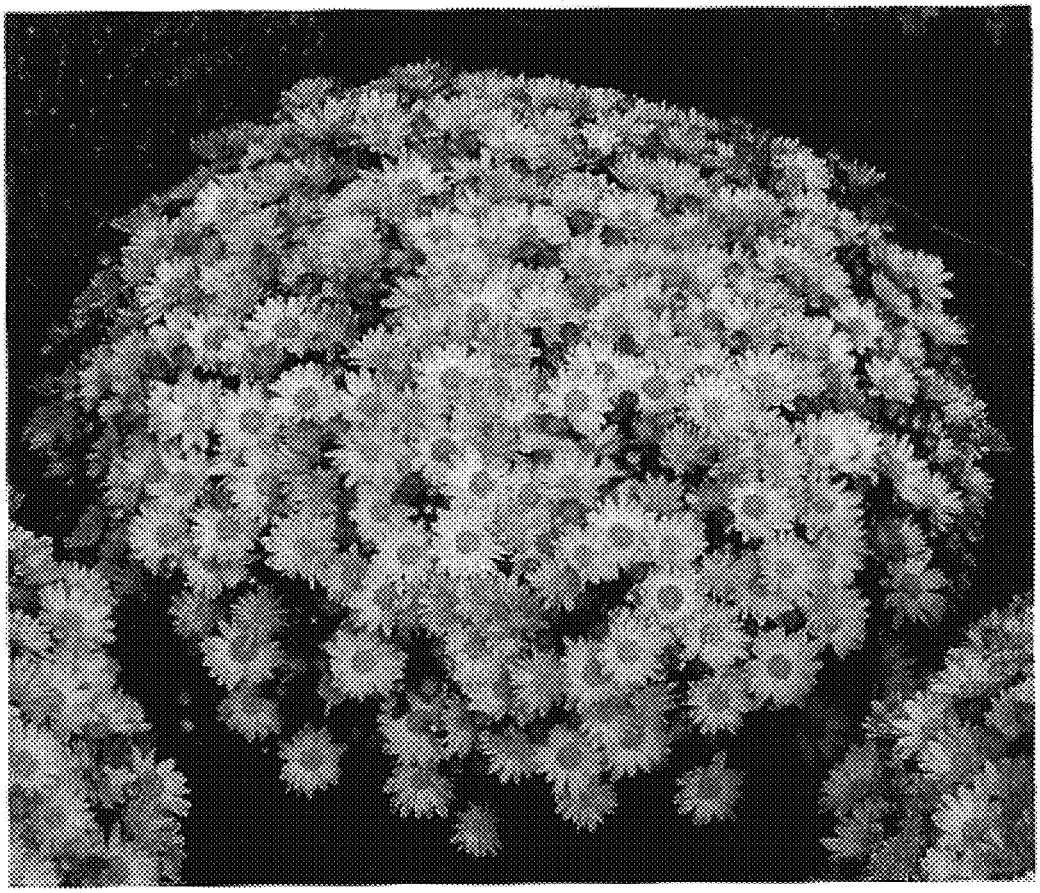

* * * * *